US009463295B2

(12) United States Patent
Kwok et al.

(10) Patent No.: US 9,463,295 B2
(45) Date of Patent: Oct. 11, 2016

(54) MASK AND MASK CUSHION THEREFOR

(71) Applicant: ResMed Limited, Bella Vista, New South Wales (AU)

(72) Inventors: Philip Rodney Kwok, Chatswood (AU); Robert Edward Styles, Glenhaven (AU)

(73) Assignee: ResMed Limited, Bella Vista (AU)

( * ) Notice: Subject to any disclaimer, the term of this patent is extended or adjusted under 35 U.S.C. 154(b) by 523 days.

(21) Appl. No.: 14/012,483

(22) Filed: Aug. 28, 2013

(65) Prior Publication Data

US 2013/0340762 A1 Dec. 26, 2013

Related U.S. Application Data

(60) Continuation of application No. 13/067,190, filed on May 16, 2011, now Pat. No. 8,522,783, which is a (Continued)

(30) Foreign Application Priority Data

Jul. 26, 1996 (AU) ...................................... PO 1265

(51) Int. Cl.
*A61M 16/06* (2006.01)
*A61M 16/00* (2006.01)
(Continued)

(52) U.S. Cl.
CPC .......... *A61M 16/0057* (2013.01); *A61B 5/097* (2013.01); *A61B 5/682* (2013.01); *A61B 5/6819* (2013.01); *A61M 16/06* (2013.01); *A61M 16/0616* (2014.02); *A61M 16/0622* (2014.02); *A61M 16/0633* (2014.02); *A61M 16/0683* (2013.01); *A61M 2210/0618* (2013.01)

(58) Field of Classification Search
CPC ........... A61M 16/06; A61M 16/0605; A61M 16/0616; A61M 16/0622; A62B 7/00; A62B 18/00; A62B 18/02; A62B 18/025
See application file for complete search history.

(56) References Cited

U.S. PATENT DOCUMENTS 781,516 A 1/1905 Guthrie
812,706 A 2/1906 Warbasse
(Continued)

FOREIGN PATENT DOCUMENTS

AU 64058/86 4/1987
AU 91/77110 B 11/1991
(Continued)

OTHER PUBLICATIONS

Interlocutory Decision in Opposition Proceedings mailed Mar. 11, 2015 in European Application No. 06 115 004.1 (EP Patent No. 1 741 461), 24 pages.

(Continued)

*Primary Examiner* — Lynne Anderson
*Assistant Examiner* — Kathryn E Ditmer
(74) *Attorney, Agent, or Firm* — Nixon & Vanderhye P.C.

(57) ABSTRACT

A cushion comprises a substantially triangularly shaped frame from which extends a membrane. The membrane is spaced away from the rim of the frame, and its outer surface is of substantially the same shape as the rim. The seal forming portion thus contacts both the surface of the wearer's nose and a portion of the wearer's face. The shape of the seal forming portion is particularly suited to effectively seal the difficult region of the facial contour that is the crease between the sides of the nose and the face.

42 Claims, 3 Drawing Sheets

Related U.S. Application Data continuation of application No. 11/826,267, filed on Jul. 13, 2007, now Pat. No. 7,950,392, which is a continuation of application No. 10/934,402, filed on Sep. 7, 2004, now Pat. No. 7,243,651, which is a continuation of application No. 10/004,428, filed on Dec. 6, 2001, now Pat. No. 6,871,649, which is a division of application No. 09/566,806, filed on May 8, 2000, now Pat. No. 6,634,358, which is a continuation of application No. 08/791,212, filed on Jan. 31, 1997, now Pat. No. 6,112,746.

(51) Int. Cl.
*A61B 5/097* (2006.01)
*A61B 5/00* (2006.01)

(56) References Cited

U.S. PATENT DOCUMENTS

| | | |
|---|---|---|
| 902,961 A | 11/1908 | Goodnow |
| 1,000,706 A | 8/1911 | Barnum |
| 1,081,745 A | 12/1913 | Johnston et al. |
| 1,105,127 A | 7/1914 | Drager |
| 1,192,186 A | 7/1916 | Greene |
| 1,632,449 A | 6/1927 | McKesson |
| 1,653,572 A | 12/1927 | Jackson |
| 1,926,027 A | 9/1933 | Biggs |
| 1,975,797 A * | 10/1934 | Montuori ............... A62B 18/00 128/205.27 |
| 2,123,353 A | 7/1938 | Catt |
| 2,166,164 A | 7/1939 | Lemberg |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lemberg |
| 2,376,871 A | 5/1945 | Fink |
| 2,387,522 A * | 10/1945 | Maurer ............... A61F 9/028 128/206.24 |
| 2,415,846 A | 2/1947 | Randall |
| 2,438,058 A | 3/1948 | Kincheloe |
| 2,578,621 A | 12/1951 | Yant |
| 2,625,155 A | 1/1953 | Engelder |
| 2,875,757 A | 1/1954 | Galleher, Jr. |
| 2,710,602 A | 6/1955 | Maybach |
| 2,931,356 A | 4/1960 | Schwarz |
| D188,084 S | 5/1960 | Garelick |
| 2,936,458 A * | 5/1960 | Luisada ............... A61F 9/027 2/435 |
| 2,939,458 A | 6/1960 | Lundquist |
| 3,013,556 A | 12/1961 | Galieher |
| 3,044,464 A | 7/1962 | Gray |
| 3,182,653 A | 5/1965 | Blount et al. |
| 3,189,027 A | 6/1965 | Bartlett |
| 3,193,624 A | 7/1965 | Webb et al. |
| 3,236,943 A | 2/1966 | Holley |
| 3,315,674 A | 4/1967 | Bloom et al. |
| 3,330,273 A * | 7/1967 | Ray ............... A61M 16/06 128/206.26 |
| 3,330,274 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,725,953 A | 4/1973 | Johnson et al. |
| 3,796,216 A | 3/1974 | Schwarz |
| 3,799,164 A | 3/1974 | Rollins |
| D231,803 S | 6/1974 | Huddy |
| 4,015,598 A | 4/1977 | Brown |
| 4,077,404 A | 3/1978 | Elam |
| D250,131 S | 10/1978 | Lewis et al. |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,305,387 A | 12/1981 | Reist-Kundig et al. |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,414,973 A | 11/1983 | Matheson et al. |
| 4,467,799 A | 8/1984 | Steinberg |
| 4,522,639 A | 6/1985 | Ansite et al. |
| 4,558,710 A | 12/1985 | Eichler |
| 4,616,647 A | 10/1986 | McCreadie |
| 4,622,964 A | 11/1986 | Flynn |
| 4,655,213 A | 4/1987 | Rapoport et al. |
| 4,658,763 A | 4/1987 | Gobien et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| 4,689,837 A * | 9/1987 | Bolle ............... A62B 18/08 2/428 |
| 4,699,092 A | 10/1987 | Ruf et al. |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,803,981 A | 2/1989 | Vickery |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,889,079 A | 12/1989 | Takeda et al. |
| 4,907,584 A | 3/1990 | McGinnis |
| 4,910,806 A | 3/1990 | Baker et al. |
| 4,919,128 A | 4/1990 | Kopala et al. |
| 4,922,921 A | 5/1990 | Donoghue |
| 4,938,210 A | 7/1990 | Shene |
| 4,938,212 A | 7/1990 | Gnook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,003,633 A | 4/1991 | Itoh |
| 5,005,571 A | 4/1991 | Dietz |
| 5,005,588 A | 4/1991 | Rubin |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,065,756 A | 11/1991 | Rapoport |
| 5,069,205 A | 12/1991 | Urso |
| D323,908 S | 2/1992 | Hollister et al. |
| 5,094,193 A | 3/1992 | Yoshikawa |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,148,802 A | 9/1992 | Sanders et al. |
| 5,159,938 A | 11/1992 | Laughlin |
| 5,178,138 A | 1/1993 | Walstrom et al. |
| D334,633 S | 4/1993 | Rudolph |
| 5,231,983 A | 8/1993 | Matson et al. |
| 5,233,978 A | 8/1993 | Callaway |
| 5,243,971 A | 9/1993 | Sullivan et al. |
| 5,265,595 A | 11/1993 | Rudolph |
| 5,279,289 A | 1/1994 | Kirk |
| 5,280,784 A | 1/1994 | Kohler |

(56) References Cited

U.S. PATENT DOCUMENTS

| | | |
|---|---|---|
| 5,297,544 A | 3/1994 | May et al. |
| 5,297,547 A | 3/1994 | Brain |
| 5,311,862 A | 5/1994 | Blasdell et al. |
| 5,322,057 A | 6/1994 | Raabe et al. |
| 5,322,059 A | 6/1994 | Walther |
| 5,323,774 A | 6/1994 | Fehlauer |
| 5,343,878 A | 9/1994 | Scarberry et al. |
| 5,349,949 A | 9/1994 | Schegerin |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,657,493 A | 8/1997 | Ferrero et al. |
| 5,657,752 A | 8/1997 | Landis et al. |
| 5,660,174 A | 8/1997 | Jacobelli |
| 5,662,101 A | 9/1997 | Ogden et al. |
| 5,666,946 A | 9/1997 | Langenback |
| 5,685,296 A | 11/1997 | Zdrojkowski et al. |
| 5,687,715 A | 11/1997 | Landis et al. |
| 5,715,814 A | 2/1998 | Ebers |
| 5,746,201 A | 5/1998 | Kidd |
| 5,813,423 A | 9/1998 | Kirchgeorg |
| 5,832,918 A | 11/1998 | Pantino |
| 5,884,624 A | 3/1999 | Barnett et al. |
| 6,082,360 A | 7/2000 | Rudolph et al. |
| 6,102,040 A | 8/2000 | Tayebi et al. |
| 6,112,746 A | 9/2000 | Kwok et al. |
| 6,357,441 B1 | 3/2002 | Kwok et al. |
| 6,412,487 B1 | 7/2002 | Gunaratnam et al. |
| 6,513,526 B2 | 2/2003 | Kwok et al. |
| 6,581,602 B2 | 6/2003 | Kwok et al. |
| 6,634,358 B2 | 10/2003 | Kwok et al. |
| 6,701,927 B2 | 3/2004 | Kwok et al. |
| 6,871,649 B2 | 3/2005 | Kwok et al. |
| 7,007,696 B2 | 3/2006 | Palkon et al. |
| 7,069,933 B2 | 7/2006 | Kwok et al. |
| 7,178,527 B2 | 2/2007 | Kwok et al. |
| 7,243,651 B2 | 7/2007 | Kwok et al. |
| 7,950,392 B2 | 5/2011 | Kwok et al. |
| 8,056,561 B2 | 11/2011 | Kwok et al. |
| 8,522,783 B2 | 9/2013 | Kwok et al. |
| 2002/0104540 A1 | 8/2002 | Kwok et al. |
| 2007/0107735 A1 | 5/2007 | Kwok et al. |
| 2012/0090618 A1 | 4/2012 | Kwok et al. |

FOREIGN PATENT DOCUMENTS

| | | |
|---|---|---|
| AU | 94/64816 B | 12/1994 |
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| CA | 1039144 | 9/1998 |
| DE | 459104 | 4/1928 |
| DE | 701 690 | 1/1941 |
| DE | 159396 | 6/1961 |
| DE | 3539073 A1 | 5/1967 |
| DE | 3015279 A1 | 10/1981 |
| DE | 3345067 A1 | 6/1984 |
| DE | 3537507 A1 | 4/1987 |
| DE | 4004157 C1 | 4/1991 |
| DE | 4343205 A1 | 6/1995 |
| DE | 19548 380 A1 | 12/1995 |
| DE | 195 48 360 A1 | 7/1996 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 | 7/1987 |
| EP | 0 264 772 | 10/1987 |
| EP | 0 252 052 | 1/1988 |
| EP | 0 264 772 | 4/1988 |
| EP | 0 303 090 B1 | 7/1988 |
| EP | 303 090 B1 | 7/1988 |
| EP | 0 386 605 A1 | 2/1990 |
| EP | 0 462 701 A1 | 5/1991 |
| EP | 0427 474 A2 | 5/1991 |
| EP | 0 462 701 | 12/1991 |
| EP | 0549 299 A2 | 6/1993 |
| EP | 0634186 A2 | 6/1993 |
| EP | 0 602 424 | 11/1993 |
| EP | 0 634 186 A2 | 6/1994 |
| EP | 0508 84 A1 | 8/1994 |
| EP | 0 597 225 | 7/1995 |
| EP | 176 925 A2 | 4/1996 |
| EP | 0 747 078 | 12/1996 |
| EP | 0 747 078 A2 | 12/1996 |
| EP | 0821 978 | 2/1998 |
| FR | 801629 | 8/1936 |
| FR | 858749 | 12/1940 |
| FR | 2 254 657 A1 | 6/1966 |
| FR | 2 658 725 A1 | 8/1991 |
| FR | 2 749 176 | 12/1997 |
| GB | 775911 | 5/1957 |
| GB | 848215 | 9/1960 |
| GB | 1395391 | 5/1975 |
| GB | 1 467 826 | 3/1977 |
| GB | 2005547 | 4/1979 |
| GB | 2145335 A | 3/1985 |
| GB | 2147506 A | 5/1985 |
| GB | 2 164 569 A | 3/1986 |
| GB | 2211098 A | 6/1989 |
| GB | 2267648 A | 12/1993 |
| IT | 326983 | 6/1935 |
| JP | 44-16955 | 7/1969 |
| JP | 54-90892 | 7/1979 |
| JP | 09/216240 A | 8/1997 |
| WO | WO 82/03548 | 10/1962 |
| WO | WO 80/01044 | 5/1980 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02180 | 2/1994 |
| WO | WO 94/6759 | 6/1994 |
| WO | WO 94/19055 | 9/1994 |
| WO | WO 94/20051 | 9/1994 |
| WO | WO 95/02428 | 1/1995 |
| WO | WO 96/11930 | 3/1996 |
| WO | WO 96/17643 | 6/1996 |
| WO | WO 96/25983 | 8/1996 |

(56) References Cited

FOREIGN PATENT DOCUMENTS

| WO | WO 96/39206 | 12/1996 |
|---|---|---|
| WO | WO 97/07847 | 3/1997 |
| WO | WO 97/41911 | 11/1997 |
| WO | WO 98/04310 | 2/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |

OTHER PUBLICATIONS

Minutes of the Oral Proceeding mailed Mar. 11, 2015 in European Application No. 06 115 004.1 (EP Patent No. 1 741 461), 12 pages.
Office Action mailed Feb. 2, 2016 in U.S. Appl. No. 14/163,945 (9 pages).
EP Communication issued in corresponding European Application No. 10 183 685.6, dated Apr. 2, 2014, 3 pages.
EP Communication issued in corresponding European Application No. 10 184 794.5, dated Apr. 2, 2014, 4 pages.
Kwok et al., U.S. Office Action issued in U.S. Appl. No. 13/293,684, dated Oct. 30, 2013, 22 pages.
Extended European Search Report mailed Feb. 25, 2016 in European Application No. 15181229.4 (6 pages).
U.S. Office Action mailed Feb. 2, 2016 in U.S. Appl. No. 14/163,945 (9 pages).
Office Action for corresponding European Application No. 10183685.6, mailed Nov. 7, 2011.
Office Action for corresponding European Application No. 10184794.5, mailed Nov. 7, 2011.
Notice of Opposition for corresponding European Application No. 06115004.1, dated Feb. 9, 2012, 27 pages.
Decision on Appeal (and English translation) completed Mar. 25, 2008 for corresponding Japanese Application No. 2005-23339, 21 pages.
Japanese Office Action and Translation for Application No. 508323/1998, Mailed Jul. 1, 2003 (6 pages).
Respironics, Inc. "Nasal Mask and Accessories Guide," Dec. 23, 1991, 6 pages.
"InterVENTions, A Ventilatory Care Newsletter," vol. 93, No. 1, Mar. 1993, Respironics, Inc., 16 pages.
"Order" from *Respironics, Inc.* v. *ResCare Limited et al.* care, Civil Action No. 95-151, with Exhibits E and G related to information allegedly available before Jul. 26, 1995, 20 pages+.
Instructions for Use for the Comfort Flap Small Child Contour Nasal Mask Accessory, Respironics Inc., Jul. 19, 1993, 2 pages.
"Comfort Flap™ Improves the Seal of Reusable Contour Nasal Masks," InterVENTions, vol. 3 No. 1, Mar. 1993, 2 pages.
Mask 1 photographs, Respironics, Inc., Reusable Full mask (small) Part # 452033, lot # 951106.
Mask 2 Photographs, Puritain-Bennett, Adam Circuit, Shell part # 231700, Swivel part # 616329-00, Pillows (medium) Part # 616324.
Mask 3 Photographs, DeVilbiss Healthcare Inc., DeVilbiss Seal-ring and CPAP Mask Kit (medium) Part # 73510-669.
Mask 4 photographs, Respironics, Inc., onarch Mini Mask With Pressure Port, part # 572004 Monarch Headgear, Part # 572011.
Mask 5 Photographs, Healthdyne Technologies, Nasal CPAP Mask (medium narrow) part # 702510.
Mask 6 Photographs, Healthdyne Technologies, Soft Series Nasal CPAP Mask, part 3702020.
Mask 7 Photographs, DeVilbiss Healthcare Inc., Small mask and Seal Rings, part # 73510-668.
Mask 8 Photographs, Respironics, Inc., Reusable Contour mask (medium), part # 302180.
Mask 9 Photographs, Healthdyne Technologies,. Healthdyne Large Headgear.
Mask 10 Photographs, Respironics, Inc., Soft cap (medium), part # 302142.
Mask 11 Photographs, Weinmann: Hamburg, Nasaimaskensystem Mit Schalldampfer (medium), Part # WN 23105.
Mask 12 Photographs, Life Care.
Mask 13 Photographs, Healthdyne Technologies.
Mask 14, King System.
Mask 15 Photographs, Respironics, Inc., Paediatric Mask.
Mask 16 Photographs, Hans Rudolph Inc., Hans Rudolph Silicone Rubber Face Mask/8900.

\* cited by examiner

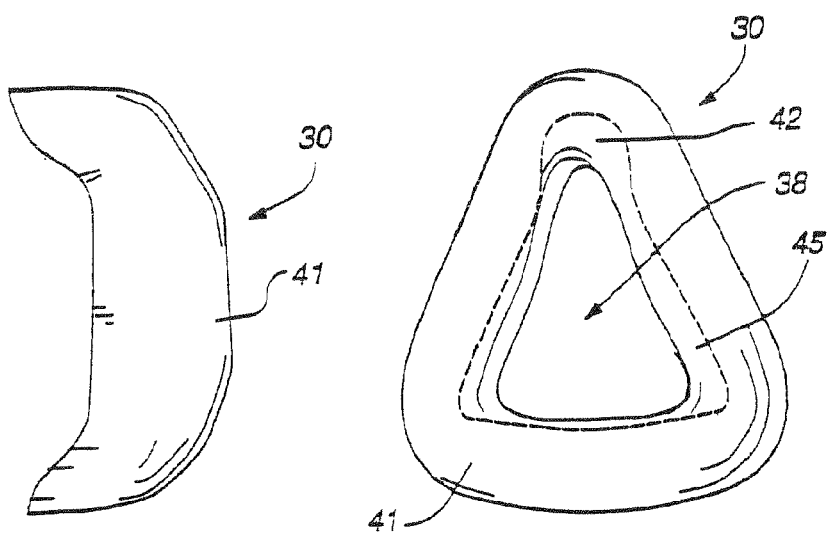
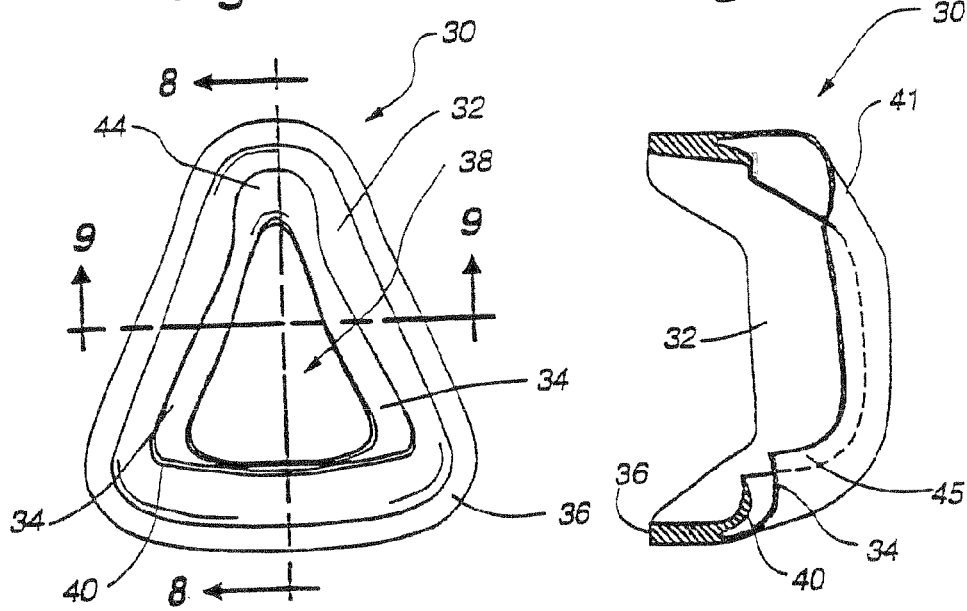
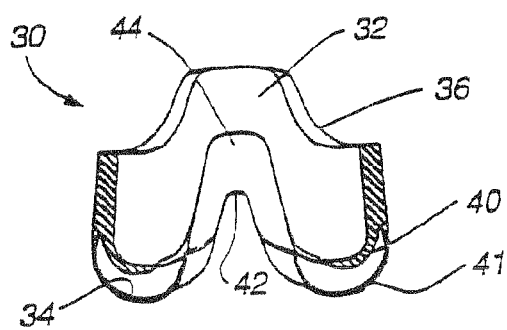
Fig. 5  Fig. 6
Fig. 7  Fig. 8
Fig. 9

MASK AND MASK CUSHION THEREFOR

CROSS-REFERENCES TO RELATED APPLICATIONS

This is a continuation of U.S. application Ser. No. 13/067,190, filed May 16, 2011, now U.S. Pat. No. 8,522,783, which is a U.S. application Ser. No. 11/826,267, filed Jul. 13, 2007, now U.S. Pat. No. 7,950,392, which is a continuation of U.S. application Ser. No. 10/934,402, filed Sep. 7, 2004, now U.S. Pat. No. 7,243,651, which is a continuation of U.S. application Ser. No. 10/004,428, filed Dec. 6, 2001, now U.S. Pat. No. 6,871,649, which is a divisional of U.S. application Ser. No. 09/566,806, filed May 8, 2000, now U.S. Pat. No. 6,634,358, which is a continuation of U.S. application Ser. No. 08/791,212, filed Jan. 31, 1997, now U.S. Pat. No. 6,112,746, which claims priority to Australian Application No. PO 1265, filed Jul. 26, 1996, each incorporated herein by reference in its entirety.

FIELD OF THE INVENTION

The invention relates generally to a nasal mask and to a cushion therefore, for example, for use in the treatment of respiratory conditions and in assisted respiration.

BACKGROUND OF THE INVENTION

Nasal masks are commonly used in the treatment of respiratory conditions and sleep disorders (e.g., obstructive sleep apnea) by delivering a flow of breathable gas for, or to assist patient respiration. These nasal masks typically receive a gas supply line which delivers gas into a chamber formed by walls of the mask. The walls usually are semi-rigid and have a face contacting portion including an aperture which is aligned with the wearer's nostrils. The face contacting portion can comprise a soft, resilient elastomeric material which may conform to various facial contours. The mask normally is secured to the wearer's head by straps. The straps are adjusted to pull the mask against the face with sufficient force to achieve a gas tight seal between the mask and the wearer's face. Gas is thus delivered to the mask and through the aperture to the wearer's nasal passages.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is that the face contacting portion may apply excessive pressure to the wearer's face resulting in discomfort and possibly skin irritation. This can occur because the face contacting portion has to distort beyond its normal range of elasticity to conform to certain facial contours which requires the application of excessive forces. In some cases these excessive pressures and forces may cause the face to distort to conform with the face contacting portion to increase wearer a discomfort, facial soreness and ulceration.

Other types of devices exist whereby small nostril nose-pieces (pillows) are held in place by a harness scrapped over the wearer's head, for example as shown in prior art U.S. Pat. No. 4,782,832 (Trimble et al). While this arrangement may alleviate some problems regarding seal breakage and skin abrasion, the harnesses associated with such devices are quite cumbersome for the wearer, as are the gas supply lines. Also, air 'jetting' into the nostrils can be irritating to the patient making such devices generally uncomfortable to use.

A further example of the prior art also is disclosed in U.S. Pat. No. 5,243,971 (Sullivan et al).

Cushion masks have also been developed. These cushion masks have an inflated cushion which provides comfort to the wearer. However, these masks, under certain circumstances, may form a tuck or pucker resulting in a leak.

It is an object of the invention to overcome or at least substantially ameliorate one or more of the foregoing disadvantages.

SUMMARY OF THE INVENTION

In one broad form, the invention discloses a nasal mask cushion to sealingly connect a mask to a wearer's face, the cushion comprising:

a substantially triangularly-shaped frame of resilient material having a rim to surround wearer's nose;

a membrane also of resilient material, said membrane being relatively more flexible than said frame, and being of the same general shape as said rim and fixed to and extending away from said frame so as to have an outer surface spaced from said rim, a portion of said outer surface forming a face contacting seal; and a nose-receiving cavity bounded by said frame and said membrane;

and wherein said seal portion is generally coterminous with respect to said rim and is resiliently deformable towards said rim in use of said cushion.

In one particularly advantageous form, the membrane is substantially saddle-shaped. The membrane further has a centrally located aperture through which the wearer's nose passes to enter said cavity.

It is preferred that the cushion and membrane each include a co-located notch to accommodate the bridge of the nose of the wearer. Typically, the seal portion contacts at least the wearer's nose, and preferably, also the facial tissue around the sides and over the bridge of the nose and between the base of the nose and the top lip.

The invention further discloses a nasal mask for connection to a wearer's face comprising:

a mask body for connection with a supply of breathable gas; and a nasal cushion, the body and cushion defining a nose-receiving cavity, said cushion including:

a substantially triangularly-shaped frame of resilient material having a rim to surround said wearer's nose;

a membrane also of resilient material, said membrane being relatively more flexible than said frame, and being of the same general shape as said rim and fixed to and extending away from said frame so as to have an outer surface spaced from said frame, a portion of said purer surface forming a face contacting seal;

and wherein said seal portion is generally coterminous with respect to said rim and is resiliently deformable towards said rim in use of said mask.

The mask body can further include attachment points from which securing straps can be attached, and by which the mask can be secured to the wearer's head. The nasal mask can yet further comprise an arm depending from said body from which a further securing strap(s) can be attached.

The invention further discloses nasal CPAP treatment apparatus comprising a flow generator for the supply of gas at a pressure elevated above atmospheric pressure to a gas delivery conduit, the conduit in turn coupled to a nasal mask as described immediately above.

In one particularly preferred form, a supply of gas can be provided to said cavity, said supply of gas assisting, but not solely causing maintenance of a seal by said seal forming portion of said membrane to the face of the wearer in use of the cushion.

Advantageously, the membrane and the rim are substantially shaped to the facial contour, and the membrane does not need to turn in on itself thus contacting the face without folds or creases. With the cushion/mask secured to the wearer's head, the headstraps need only to be tensioned to balance the force due to mask gas pressure that tends to lift the mask off the face. Such relatively lower mask-to-face pressure results is in greater patient comfort, and a reduction in the likelihood of skin irritation.

BRIEF DESCRIPTION OF THE DRAWINGS

An embodiment of the invention will now be described with reference to the accompanying drawings, in which:

FIG. 5 is a side view of the mask cushion;

FIG. 6 is a front view of the mask cushion;

FIG. 7 is a rear view of the mask cushion;

FIG. 8 is a sectional view along section lines 8-8 of FIG. 7; and

FIG. 9 is a sectional view along section lines 9-9 of FIG. 7.

DETAILED DESCRIPTION OF PREFERRED EMBODIMENTS

Figure 1:
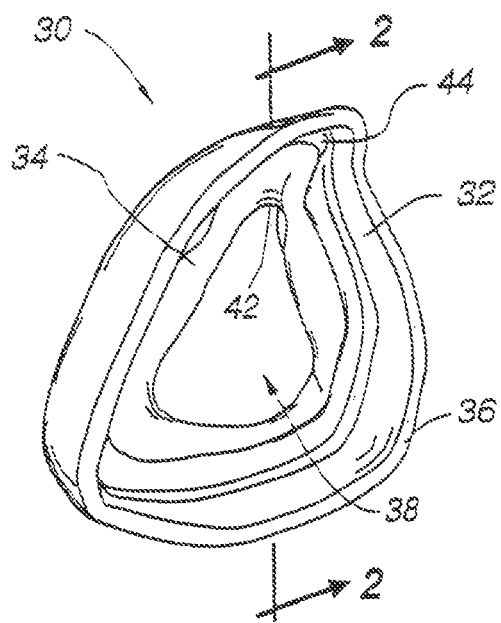
FIG. 1 is a rear perspective view of a mask cushion embodying the present invention.
Figure 2:
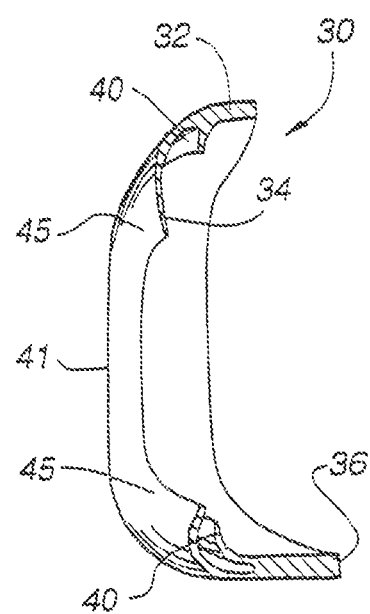
FIG. 2 is a cross-sectional view along line 2-2.

FIG. 1 shows a perspective view of a nasal cushion 30 embodying the invention. FIG. 2 shows the cross-sectional view along line 2-2. Referring to FIGS. 1-2 and 5-9, the cushion 30 comprises a substantially triangularly shaped frame 32 from which extends a membrane 34. The frame 32 has a scalloped edge 36 by which the cushion 30 is affixed to a mask body, as presently will be described.

The membrane 34 has an aperture 38 into which the wearer's nose is received in use of the cushion 30. The membrane 34 is spaced away from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42, 44 that receive the bridge of the wearer's nose in use of the cushion 30.

As is best seen in FIG. 2, the frame 32 and the membrane 34 are integrally formed, typically by in a one-shot molding process. The frame 32 and the membrane 34 are fabricated from a resilient material. One suitable such material is SILASTIC™ silicone elastomer manufactured by Dow Corning. The frame 32, is one preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the cushion 30, a wearer's nose will be inserted in the aperture 38 to engage a seal forming portion 45 (formed between the dashed lines of FIG. 3) of the outer surface 41 to cause deformation of the membrane 34. Depending upon the securing force supplied to the membrane 34, it may deform to a point where it butts against the rim 40 of the frame 32. The frame 32 has a rigidity sufficient to withstand usual securing pressures in use of the cushion 30 to tend to retain its shape and resist deformation. It thus acts as a supporting structure.

Figure 3:
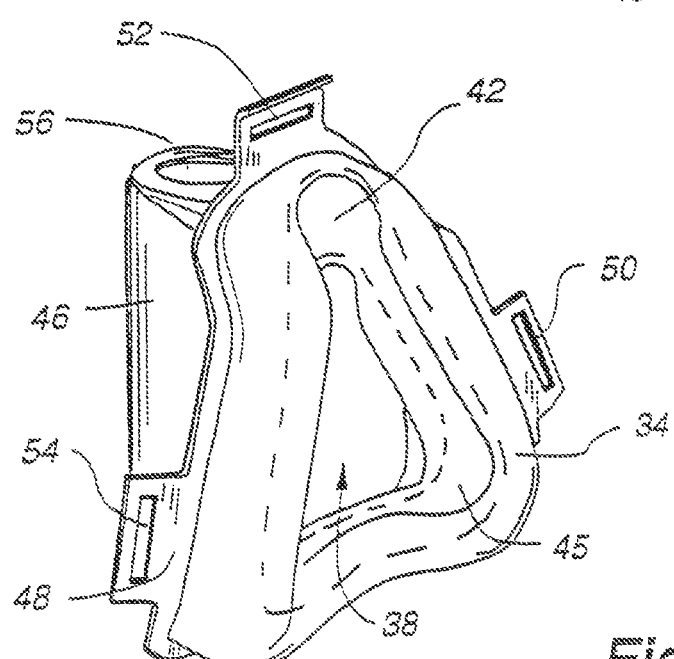
FIG. 3 is a perspective view of a nasal mask including the cushion of FIGS. 1 and 2.

Referring now to FIG. 3, the nasal cushion 30 is shown attached to a mask body 46 by the edge 36 of the frame 32, adhered or otherwise secured to a flange 48 of the mask body 46. Only the outer surface 41 of the membrane 34 can be seen. The flange 48 includes three slots 50, 52, 54 from which tensioning straps can be attached to secure the cushion 30 and the mask body 46 (in combination) to the head of a wearer.

The mask body 46 forms a cavity that can receive the nose of the wearer by the aperture 38. A port 56 is provided at the top of the mask body 46 by which breathable gas can be supplied to the chamber.

Figure 4:
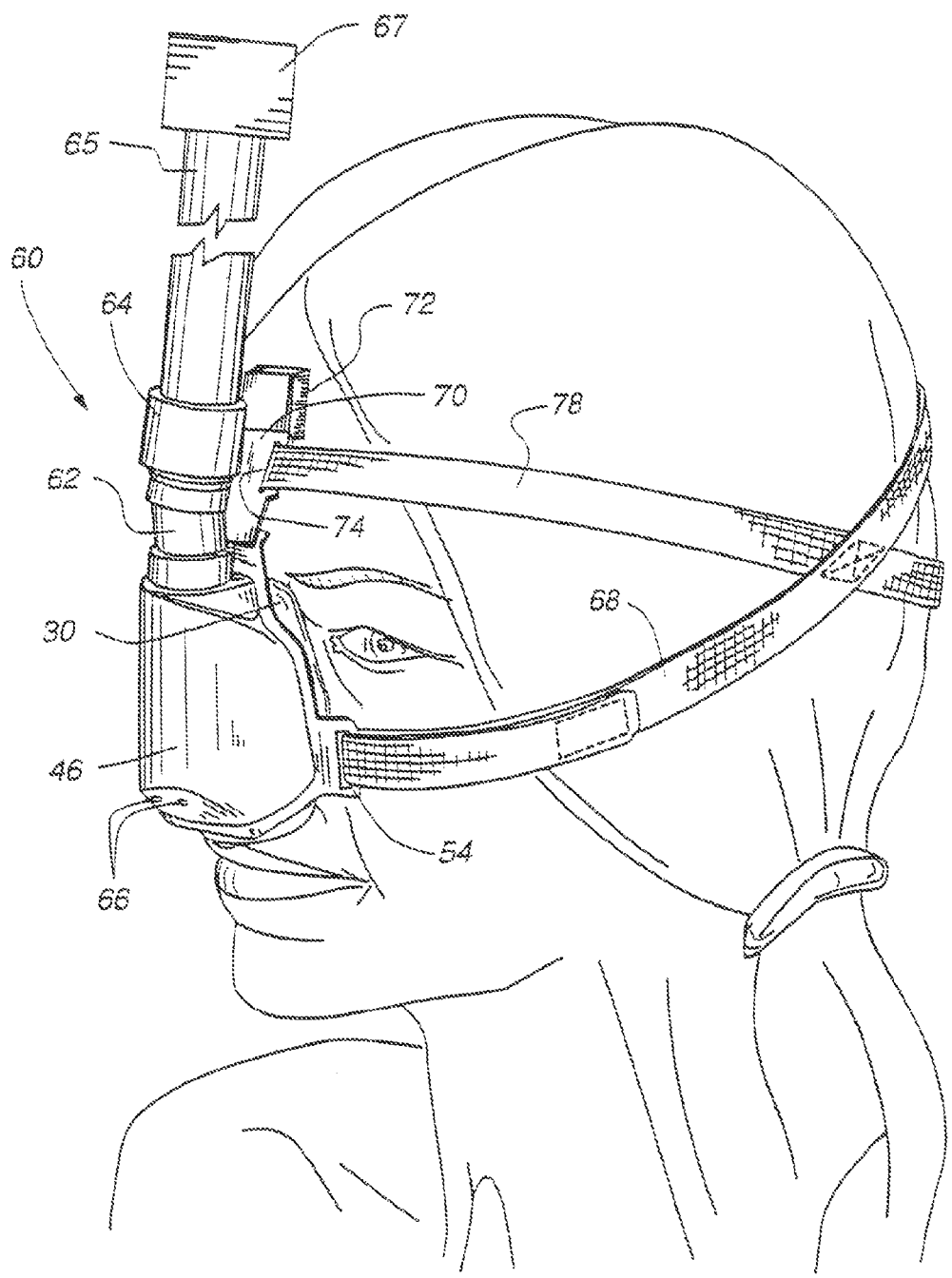
FIG. 4 is a perspective view of the nasal mask of FIG. 3 secured to a wearer's head.

Referring now to FIG. 4, there is shown a nasal mask 60 including the mask body 46 and the mask cushion 30. A coupling tube 62 is connected at one end with the inlet port 56, and at the other to a socket 64 into which can be received a gas delivery tube 65 for the supply of breathable gas to the chamber internal of the mask body 46. The mask body 46 from a flow generator 67 also has two vent openings 66 by which expired gas is exhausted. A first fastening strap 68 is fixed between to the lower two slots 50, 54. The upper slot 52 receives an arm 70, the top end of which has a resilient pad 72 to engage the forehead of the wearer. The arm 70 has two slots 74 (only one slot shown in FIG. 4) along its side edges, by which a second fastening strap 78 is secured.

In fitting the nasal mask 60, the wearer's nose is received through the aperture 38 into the chamber within the mask body 46. The seal forming portion 45 thus contacts both the surface of the wearer's nose and a portion of the wearer's face in the region between the base of the nose and the upper lip, and around the sides and over the bridge of the nose. The shape of the seal forming portion 45 is particularly suited to effectively seal the difficult region of the facial contour that is the crease between the sides of the nose and the face. Depending upon the tension applied by the fastening straps 68, 78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. On relative movement of the mask 60 in relation to the wearer's head, the nose will be restrained by contacting the frame 32. Thus only limited relative motion between the mask 60 and the wearer's nose and face occurs.

The membrane 34 closely imitates the facial contour, and because of its relatively lesser stiffness than the frame 32, can conform to particular facial structures with minimum force, and without a tendency to fold or crease.

If the fastening strap 68,78 are tensioned to excess, the membrane 34 deforms to abut the rim 40 of the cushion 32, the frame 32 thus acting as an "end limit". In such a configuration, almost zero relative movement can occur between the mask 60 and the wearer's head.

The nasal cushion 30 and nasal mask 60 has been described with reference to CPAP or assisted respiration treatment, however it is to be understood that the invention generally is applicable to any application where gas and/or atomised liquid is to be supplied to the entrance of the nasal airways. Such applications include nebulisers, gas masks and anaesthetic machines.

The invention claimed is:

1. A mask cushion to sealingly connect a mask to a wearer's face, the cushion comprising:
   a frame of resilient material having a rim to at least partially surround the wearer's nose; and
   a membrane also of resilient material and defining an aperture sized to receive the wearer's nose, said membrane being thinner than and relatively more flexible than said frame, said membrane being fixed to and extending away from said frame so as to be spaced from said rim by a gap, said membrane having an outer surface forming a face contacting seal portion that is pre-shaped to generally match the contours of the wearer's face, wherein the face contacting seal portion is structured such that it is not required to turn in on itself to conform with the wearer's face, in use;
   wherein:
   the cushion at least partly forms a breathing chamber to receive pressurized breathable gas, for delivery to at least a nasal passage of the wearer, the breathing chamber being accessible by the wearer via the aperture of the membrane;
   the rim and the membrane are commonly curved towards the breathing chamber,
   the cushion is structured so that the pressurized gas in the chamber assists in maintaining a seal between the membrane and the wearer in use;
   the frame and rim are structured to resist deformation so as to form a support structure for the membrane,
   said membrane is resiliently deformable towards said gap to abut said rim in use of said cushion; and
   the rim and the membrane have a pre-formed co-located notch to accommodate the bridge of the wearer's nose.

2. A cushion as claimed in claim 1, wherein said membrane and said rim are substantially saddle-shaped.

3. A cushion as claimed in claim 2, wherein said membrane is shaped so that said seal portion, in use, contacts at least the wearer's nose.

4. A cushion as claimed in claim 3, wherein said seal portion, in use, contacts the facial tissue around the sides and over the bridge of the nose, and between the base of the nose and the top lip.

5. A cushion as claimed in claim 1, wherein said rim and said seal portion are pre-shaped to generally match facial contours in the region of facial tissue around the sides and over the bridge of the nose, and between the base of the nose and the top lip.

6. A cushion as claimed in claim 1, wherein the face contacting seal portion is pre-shaped to closely imitate the contours of the wearer's face.

7. A cushion as claimed in claim 1, wherein the face contacting seal portion is structured to enable contact with the wearer's face without folds or creases.

8. A cushion as claimed in claim 1, wherein the membrane is less stiff than the frame, to conform with the wearer's facial structure with minimum force, without a tendency to fold or crease.

9. A mask for connection to a wearer's face comprising:
   a mask body for connection with a supply of breathable gas;
   a cushion, the body and cushion defining a nose-receiving cavity adapted to receive pressurized gas for breathing by the wearer in use;
   at least one securing strap to secure the mask body and cushion to the wearer's head, the strap being structured to be tensioned to balance force due to the pressurized gas that tends to lift the mask off of the wearer's face; and
   at least one vent opening by which gas expired by the wearer is exhausted to atmosphere;
   wherein the cushion includes:
   a frame of resilient material having a rim to surround at least a portion of the wearer's nose;
   a membrane also of resilient material, said membrane being thinner than and relatively more flexible than said frame, the membrane being fixed to and extending away from said frame so as to be spaced from said rim by a gap, said membrane having an outer surface forming a face contacting seal portion that is pre-shaped to generally match the contours of the wearer's face, wherein the face contacting seal portion is structured such that it is not required to turn in on itself to conform with the wearer's face, in use;
   wherein:
   the rim and frame are curled inwardly towards the nose-receiving cavity and structured to resist deformation so as to form a support structure for the membrane, and
   said seal portion is resiliently deformable towards said gap to abut said rim in use of said mask, depending on the facial contours of the wearer and/or strap tension applied the at least one securing strap; and
   said membrane and said rim each have a co-located notch to accommodate the bridge of a nose.

10. A mask as claimed in claim 9, wherein said mask body includes at least one attachment point to which the at least one securing strap is coupled.

11. A mask as claimed in claim 9, wherein said membrane is shaped so that said seal portion, in use, contacts at least the wearer's nose.

12. A mask as claimed in claim 11, wherein said seal portion, in use, contacts the facial tissue around the sides and over the bridge of the nose, and between the base of the nose and the top lip.

13. A mask as claimed in claim 9, wherein said rim and said seal portion are shaped to generally match facial contours in the region of facial tissue around the sides and over the bridge of the nose, and between the base of the nose and the top lip.

14. A mask cushion to sealingly connect a mask to a wearer's face, the cushion comprising:
   a frame of resilient material having a rim shaped to generally match facial contours at least in the region of facial tissue around the sides of the nose, and between the base of the nose and the top lip;
   a membrane also of resilient material, the membrane being thinner than and relatively more flexible than the frame, said membrane being fixed to and extending away from the frame so as to be spaced from the rim by a gap, said membrane having an outer surface forming a face contacting seal portion that is pre-shaped to generally match the contours of the wearer's face, the membrane including a pre-formed notch to accommodate the wearer's nose bridge, wherein the face contacting seal portion is structured such that it is not required to turn in on itself to conform with the wearer's face, in use; and wherein the rim and the membrane are inwardly curled in a common orientation towards the wearer's nose in use, and a strap structured to secure the cushion to the wearer's face, wherein, before application of strap tension, the seal portion is spaced from the rim of the cushion by the gap, and as a result of application of strap tension and/or to accommodate the wearer's facial contours, the seal portion is resiliently deformable into said gap to abut against the rim, said membrane resiliently returning to its original position, spaced from said rim by said gap, when the mask cushion is not in use.

15. A mask cushion for sealingly connecting a mask to a patient's face during the administration of positive airway pressure, the cushion including:

a frame of resilient material, said frame having a rim to surround at least a portion of the patient's face;

a membrane of resilient material and fixed to and extending away from the frame so as to be spaced from the rim, in at least one region of the frame, so as to include a gas-filled gap between the membrane and the rim before the cushion is in use, said membrane fully covering or overlying the rim as seen in cross section, wherein each of the rim and the membrane includes a distal end that is unsupported, the distal ends curled inwardly and terminating in a substantially common orientation, a seal forming portion on an outer surface of said membrane, said seal forming portion being provided only on said membrane such that only the membrane forms a seal with the patient's face in use; the membrane being pre-shaped to generally match the contours of the patient's face including a preformed contoured notch to accommodate the bridge of the patient's nose, wherein the seal forming portion is structured such that it is not required to turn in on itself to conform with the patient's face, wherein the frame and the membrane at least partly define a breathing cavity to receive pressurized gas for delivery to at least a nasal airway of the patient, the membrane having an aperture comprised to receive the patient's nose and allow the pressurized gas to flow from the breathing cavity to the patient's nasal airway.

16. A mask cushion as claimed in claim 15, wherein said seal forming portion is resiliently deformable into the gap towards the rim in use of the cushion.

17. A mask cushion as claimed in claim 15, wherein said rim has a preformed and contoured notch, co-located relative to the notch of the membrane, also to accommodate the bridge of the patient's nose.

18. A mask cushion as claimed in claim 15, wherein said membrane is shaped so that said seal forming portion, in use, contacts at least a patient's nose.

19. A mask cushion as claimed in claim 15, wherein the seal forming portion, in use, contacts the facial tissue around the sides and over the bridge of the nose, and between the base of the nose and the top lip.

20. A mask cushion as claimed in claim 15, wherein said rim and said seal forming portion are pre-shaped to generally match facial contours of the facial tissue around the sides and over the bridge of the nose, and between the base of the nose and the top lip.

21. A mask cushion as claimed in claim 15, wherein the frame, the rim and the membrane are formed as a one piece unit.

22. A mask cushion as claimed in claim 15, wherein the rim has a thickness that is greater than a thickness of the membrane.

23. A mask cushion as claimed in claim 22, wherein the rim is about four times thicker than the membrane.

24. A mask cushion as claimed in claim 22, wherein the rim thickness is about 1.5 mm, and the membrane thickness is about 0.35 mm.

25. A mask cushion as claimed in claim 15, further comprising a strap structured to secure the cushion to the patient's face, wherein, before application of strap tension, the seal forming portion is spaced from the rim of the cushion by said gap, and during application of strap tension and/or depending on the patient's contours, the seal forming portion deforms to abut against the rim of the cushion.

26. A mask cushion as claimed in claim 15, wherein the membrane is formed of silicone.

27. A mask cushion as claimed in claim 15, wherein the membrane is molded.

28. A mask cushion as claimed in claim 15, wherein the membrane is molded to generally match the contours of the patient's face even when the mask is not in use.

29. A mask cushion as claimed in claim 15, wherein the outer surface of the membrane is substantially the same shape as the rim of the frame in the at least one region.

30. A mask cushion as claimed in claim 15, wherein the gap is formed between the frame and the membrane in the lip region of the wearer, whereby the membrane may resiliently deform into the gap toward the frame in use of the cushion.

31. A mask cushion as claimed in claim 15, wherein the rim of the frame is designed to define a maximum deformation position of the membrane in normal use.

32. A mask cushion as claimed in claim 15, further comprising a strap structured to secure the cushion to the patient's face, wherein the outer surface forms a seal upon connection to the patient's face and application of minimal force, if any, to the strap.

33. A mask cushion as claimed in claim 15, wherein the rim of the frame is approximately 1.5 mm thick.

34. A mask cushion as claimed in claim 15, wherein the membrane is approximately 0.35 mm thick.

35. A mask cushion as claimed in claim 15, wherein the frame is formed of silicone.

36. A mask cushion as claimed in claim 15, wherein frame is molded.

37. A mask cushion as claimed in claim 15, wherein said rim is structured to resist deformation so as to form support structure for the membrane.

38. A mask comprising the mask cushion as claimed in claim 15, said mask including a mask body for connection with a supply of pressurized breathable gas.

39. A mask as claimed in claim 38, wherein the mask further includes at least one vent opening by which gas expired by the patient is exhausted to atmosphere.

40. A mask as claimed in claim 38, wherein said mask body includes attachment points.

41. A mask as claimed in claim 40, further comprising securing straps fixed to said attachment points.

42. A CPAP treatment apparatus comprising the mask as claimed in claim 38, the CPAP treatment apparatus including a flow generator for the supply of gas at a pressure elevated above atmospheric pressure; and a gas delivery conduit coupled to said flow generator.

* * * * *